(12) United States Patent
Peera et al.

(10) Patent No.: US 8,697,915 B2
(45) Date of Patent: Apr. 15, 2014

(54) DIAMINO-ALCOHOL COMPOUNDS AND PROCESSES FOR THEIR MANUFACTURE

(75) Inventors: Asghar A. Peera, Buffalo Grove, IL (US); Ian A. Tomlinson, Midland, MI (US)

(73) Assignees: ANGUS Chemical Company; Dow Global Technologies LLC

( * ) Notice: Subject to any disclaimer, the term of this patent is extended or adjusted under 35 U.S.C. 154(b) by 82 days.

(21) Appl. No.: 12/928,583

(22) Filed: Dec. 15, 2010

(65) Prior Publication Data

US 2011/0152574 A1    Jun. 23, 2011

Related U.S. Application Data

(60) Provisional application No. 61/284,638, filed on Dec. 22, 2009.

(51) Int. Cl.
C07C 209/00 (2006.01)
C07C 213/00 (2006.01)
C07C 217/00 (2006.01)

(52) U.S. Cl.
USPC .......................................... 564/495; 564/356

(58) Field of Classification Search
None
See application file for complete search history.

(56) References Cited

U.S. PATENT DOCUMENTS

| 2,363,464 | A | * | 11/1944 | Senkus | 564/495 |
| 2,475,996 | A | * | 7/1949 | Smith | 568/704 |
| 3,112,345 | A | | 11/1963 | Stansbury, Jr. et al. | |
| 3,534,112 | A | * | 10/1970 | Tindall | 568/712 |
| 5,227,198 | A | * | 7/1993 | Laura et al. | 427/373 |

FOREIGN PATENT DOCUMENTS

WO    2004105963 A1    12/2004

OTHER PUBLICATIONS

Luzzio et al. Tetrahedron 57 (2001) 915-945.*
Hayashi et al. Org. Lett. 2007, vol. 9, No. 25, 5307-5309.*
Senkus, Iron Reduction of Some Aliphatic Nitro Compounds, Industrial & Engineering Chemistry, vol. 40, No. 3, 1948, pp. 506-508.
Lindstedt, et al., The Journal of Organic Chemistry, vol. 28, No. 1, 1963, pp. 251-252.
Kolter, et al., Synthesis of Sphinganine Analogues Modified in the Head Group, Tetrahedron, vol. 50, No. 47. 1994, pp. 13425-13432.
Singh, et al., Efficient Asymmetric Synthesis of the Vasopeptidase Inhibitor BMS-189921, Org. Lett., vol. 5, No. 17, 2003, pp. 3155-3158.
European Search Report for EP10194224.1 dated Dec. 22, 2011.

* cited by examiner

Primary Examiner — Clinton Brooks

(57) ABSTRACT

A new class of compounds, namely diamino alcohols, is described, along with a process for their production and their use as dispersing additives for coating formulations.

3 Claims, 1 Drawing Sheet

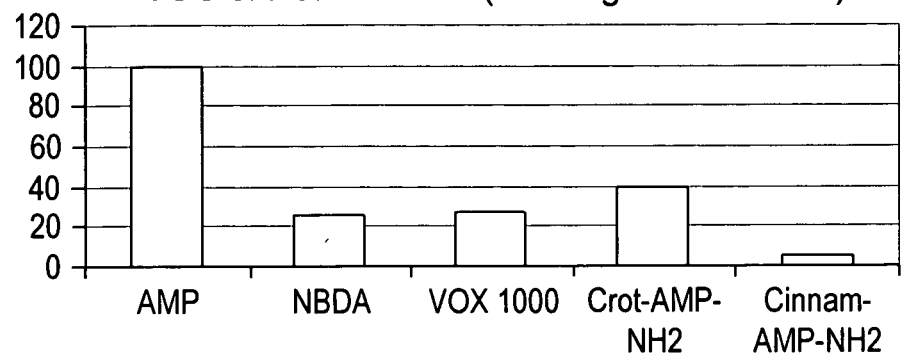
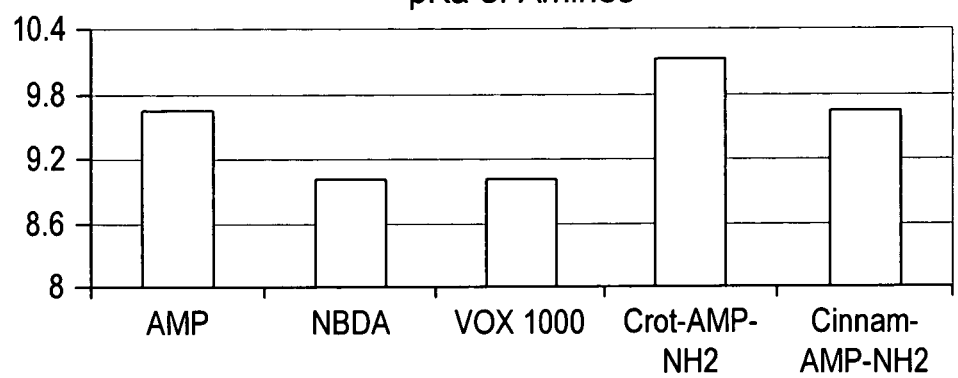

DIAMINO-ALCOHOL COMPOUNDS AND PROCESSES FOR THEIR MANUFACTURE

This application claims the benefit of priority under 35 U.S.C. §119(e) of U.S. Provisional Patent Application No. 61/284,638 filed on Dec. 22, 2009.

FIELD OF THE INVENTION

The present invention relates to a new class of compounds, namely diamino alcohols, a process for producing same, and their uses as dispersants in coating formulations.

BACKGROUND OF THE INVENTION

Simple amine compounds are known to provide neutralizing, dispersant and hardening properties when added to coatings, mineral slurries and epoxy formulations. Methods for simple amine compound manufacture are well-documented and known in the art, and when the goal is to prepare primary amines, the preferred routes often involve intermediate nitro alcohol compounds. For various reasons, it would be advantageous to have compounds with more than one amino group and low volatile organic compound ("VOC") content.

Volatile organic compounds are organic chemical compounds that have high enough vapor pressures under normal conditions (i.e., 1 atmosphere and 25° C.) to significantly vaporize and enter the atmosphere. They include a variety of chemicals, many of which have adverse health effects, and are emitted by a wide variety of products including but not limited to: paints and lacquers, paint strippers, cleaning supplies, pesticides, building materials and furnishings, office equipment such as copiers and printers, correction fluids and carbonless copy paper, graphics and craft materials including glues and adhesives, permanent markers, and photographic solutions. Minimization of VOC content has become the focus of public attention as well as government regulation.

Processes for the manufacture of the intermediate nitro alcohol compounds, are known and typically involve nitro aldol reaction (Henry Reaction) between nitroalkanes and aldehydes. There has been occasional reference to the preparation of dinitro alcohols involving a tandem Michael addition and Henry reaction of a nitroalkane with an α,β-unsaturated aldehyde. For example, see "Secondary dinitro alcohols," Smith, Curtis W. (Shell Development Co.) 1949, and U.S. Pat. No. 2,475,996, which describe the manufacture of the nitro alcohol 2,5,6-trimethyl-2,6-dinitro-3-heptanol. This nitro alcohol is also prepared as an intermediate to making a vasopeptidase inhibitor, as discussed in Efficient Asymmetric Synthesis of the Vasopeptidase Inhibitor BMS-189921 by Janak Singh et al., Org. Lett. (2003), 5, 17, 3155-3158. In addition, manufacture of the nitro alcohol compound 2,6-dinitro-5-phenyl-heptan-3-ol has been described in David St. Clair Black et. al. Australian Journal of Chemistry, 1976, 29(11), 2511. As is also well-established, nitro alcohol compounds may be readily converted to the aminoalcohol compounds by hydrogenation with hydrogen over a suitable catalyst, for example Raney nickel or a platinum- or palladium-based catalyst (Pt or Pd in elemental form or as oxides, with or without supports, e.g., carbon). Those skilled in the art are also aware that other reducing agents which will reduce nitroalkanes to primary amines include metal/acid combinations, e.g., iron/acetic acid; and aluminum hydrides. The preferred reducing agents include hydrogen gas in combination with any of the following catalysts: Raney nickel, platinum or palladium.

Diamino alcohol compounds and their uses, on the other hand, are not currently represented in the prior art.

SUMMARY OF THE INVENTION

The present invention provides a diamino alcohol compound having the formula:

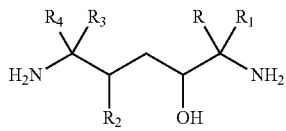

wherein R is independently hydrogen, alkyl, aryl, or —CH$_2$OH; R$_1$ is independently hydrogen, alkyl, or —CH$_2$OH; alternatively, R and R$_1$ may be linked together to form a cycloalkyl; R$_2$ is independently hydrogen, methyl, alkyl, phenyl or substituted phenyl; R$_3$ is independently hydrogen, alkyl, phenyl or substituted phenyl, or —CH$_2$OH; R$_4$ is independently hydrogen, alkyl, or —CH$_2$OH; and alternatively, R$_3$ and R$_4$ may be linked together to form a cycloalkyl.

The present invention also provides a process for the production of the aforesaid diamino alcohol compound, comprising reacting (1) a primary or secondary nitroalkane and (2) an α, β-unsaturated aldehyde to form a dinitro alcohol; and then further reduce the nitro alcohol to the corresponding diamino alcohol under hydrogenation conditions and in the presence of a catalyst. The reaction is performed under conditions in which Michael addition of the nitroalkane occurs more rapidly than the Henry reaction, allowing for the sequential reactions to produce a dinitroalcohol. The (1) nitroalkane and the (2) aldehyde are provided at a molar ratio of 2:1 during the first reaction step which produces the dinitro alcohol. The primary or secondary nitroalkane may be a C$_1$-C$_{20}$ nitroalkane. The α, β-unsaturated aldehyde may be selected from the group consisting of: acrolein, crotonaldehyde and cinnamaldehyde.

Where the desired product is a diamino poly-alcohol compound, the (1) nitroalkane is a primary nitroalkane and the process for production of the diamino poly-alcohol compound further comprises, after reacting the (1) primary nitroalkane and (2) α, β-unsaturated aldehyde, but prior to reducing the resulting nitro alcohol, further reacting the resulting nitro alcohol with (3) an aldehyde, such as formaldehyde, to form a dinitro poly-alcohol compound, which is then further reduced under hydrogenation conditions and in the presence of a catalyst.

BRIEF DESCRIPTION OF THE DRAWINGS

A more complete understanding of the present invention will be gained by reference to the accompanying FIGURE which provides bar graphs showing the VOC content and pKa of neat diamino alcohols of the present invention compared with those of other commercially available amine compounds.

DETAILED DESCRIPTION OF THE INVENTION

A new and useful class of amino compound, namely diamino alcohols, has been discovered, along with processes for their manufacture. These compounds are produced by tandem Michael and Henry reaction of nitroalkanes with one or more α, β-unsaturated aldehydes and, optionally, post reacted with an aldehyde such as formaldehyde. As a result, the diamino alcohol compounds produced have primary amine groups, preferably bonded to tertiary carbon atoms, with low content of volatile organic compounds (VOCs). They may be represented by the following formula:

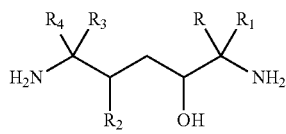

wherein R is independently hydrogen, alkyl, aryl, or —CH$_2$OH; R$_1$ is independently hydrogen, alkyl, or —CH$_2$OH; alternatively, R and R$_1$ may be linked together to form a cycloalkyl; R$_2$ is independently hydrogen, methyl, alkyl, phenyl or substituted phenyl; R$_3$ is independently hydrogen, alkyl, phenyl or substituted phenyl, or —CH$_2$OH; R$_4$ is independently hydrogen, alkyl, or —CH$_2$OH; and alternatively, R$_3$ and R$_4$ may be linked together to form a cycloalkyl.

The foregoing category of diamino alcohols includes various degrees of poly-alcohols ("polyols") as well as simple diamino mono-alcohols. The simpler diamino mono-alcohols would have the following formula:

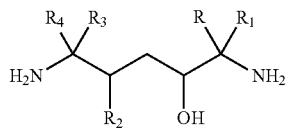

wherein R is independently hydrogen, alkyl, phenyl or substituted phenyl; R$_1$ is independently hydrogen or alkyl; alternatively, R and R$_1$ may be linked together to form a cycloalkyl; R$_2$ is independently hydrogen, alkyl, or phenyl or substituted phenyl; R$_3$ is independently hydrogen, alkyl, or aryl; R$_4$ is independently hydrogen or alkyl; and alternatively, R$_3$ and R$_4$ may be linked together to form a cycloalkyl.

The diamino mono-alcohols of the present invention may be produced by reaction of a nitroalkane and an α, β-unsaturated aldehyde which produces an intermediate dinitro alcohol compound. This reaction is typically operated at temperatures between 0° C. and 100° C. under atmospheric pressure, for example, without limitation between 0° C. and 50° C. Applicants have surprisingly and conveniently found that this reaction proceeds sequentially with Michael addition of nitroalkane to the olefin occurring first, followed by aldol (Henry) reaction in which the second nitroalkane is added to the aldehyde, to produce a single species of dinitro mono-alcohol intermediate.

The nitroalkane may be a primary or secondary nitroalkane having the formula:

wherein R is hydrogen, R$^1$ is hydrogen, alkyl, phenyl or substituted phenyl; or wherein R is alkyl, phenyl, or substituted phenyl, and R$^1$ is alkyl, or R and R$^1$ may be linked together to form a cycloalkyl. For example, without limitation, nitromethane, nitroethane, 2-nitropropane, nitrocyclohexane etc. are all suitable nitroalkanes for use as starting materials to prepare the diamino alcohol compounds in accordance with the present invention. More particularly, the primary or secondary nitroalkane may be a C$_1$-C$_{20}$ nitroalkane, a C$_1$-C$_{10}$ nitroalkane, or even a C$_2$-C$_6$ nitroalkane.

Suitable α, β-unsaturated aldehydes have the following formula:

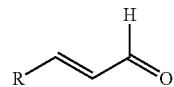

wherein R is hydrogen, methyl (alkyl), phenyl, or substituted phenyl. Suitable unsaturated aldehydes include, but are not limited to, acrolein, crotonaldehyde, cinnamaldehyde, derivatives of cinnamaldehyde substituted at the aromatic ring, etc.

The foregoing sequential Michael-Henry reaction between the nitroalkane and unsaturated aldehyde occurs in the presence of a suitable catalyst including, but not limited to, organic bases such as 1,8-Diazabicyclo[5.4.0]undec-7-ene ("DBU"), 2-dimethylamino-2-methyl-1-propanol ("DMAMP"), trimethylamine (TMA), dimethylisopropylamine (DMIPA), N,N,N',N'-tetramethylguanidine (TMG), Verkade's base, etc. Alternatively, inorganic bases such as potassium carbonate, and sodium hydroxide may also be used as catalysts for the sequential Michael-Henry reaction described above.

The starting materials are provided at a molar ratio of nitroalkane to aldehyde of typically 2:1. The reaction may be performed with or without a solvent, according to the preference of the practitioner. Suitable solvents include but are not limited to tetrahydrofuran, 2-methyltetrahydrofuran, dioxane.

Where the desired product is a diamino poly-alcohol compound, the (1) nitroalkane is a primary nitroalkane and the process for production of the diamino poly-alcohol compound further comprises, after reacting the (1) primary nitroalkane and (2) α, β-unsaturated aldehyde, but prior to reducing the resulting nitro alcohol, further reacting the resulting nitro alcohol with (3) an aldehyde, such as formaldehyde, to form a dinitro poly-alcohol compound, which is then further reduced under hydrogenation conditions and in the presence of a catalyst.

More particularly, the production of diamino poly-alcohol (polyol) compounds proceeds as follows: (A) reacting (1) a primary nitroalkane and (2) an α, β-unsaturated aldehyde to form a dinitroalcohol; (B) further reacting the dinitroalcohol with (3) an aldehyde, such as formaldehyde, to form a dinitro poly-alcohol (e.g., a dintro-dialcohol or dinitro-trialcohol) product; and (C) then further reducing the dinitro poly-alcohol product to the corresponding diamino poly-alcohol product under hydrogenation conditions, in the presence of a catalyst. The reaction is performed under conditions in which the Michael addition of the nitroalkane occurs more rapidly than the Henry reaction (i.e., temperatures between 0° C. and 100° C. under atmospheric pressure, for example, without limitation, between 0° C. and 50° C.), allowing for the sequential reactions to produce the dinitro poly-alcohol. The (1) nitroalkane and the (2) aldehyde are provided at a molar ratio of 2:1 during the first reaction step which produces the dinitro alcohol. The primary nitroalkane may be a primary $C_1$-$C_{20}$ nitroalkane, for example, without limitation, a primary $C_1$-$C_{10}$ nitroalkane. The α, β-unsaturated aldehyde may be selected from the group consisting of: acrolein, crotonaldehyde, cinnamaldehyde, and derivatives of cinnamaldehyde substituted at the aromatic ring.

The subsequent reaction of the dinitro alcohol with a second aldehyde, such as formaldehyde, occurs after the completion of the reaction to form the nitro alcohol has been confirmed (e.g, such as by analytical methods known to persons of ordinary skill in the art including, but not limited to, gas chromatography or high-performance liquid chromatography). The ratio of the formaldehyde to the dinitro alcohol is typically 2:1 for this sequential reaction step. Again, this reaction may be performed with or without a solvent, according to the preference of the practitioner, such as, without limitation, tetrahydrofuran, 2-methyltetrahydrofuran, dioxane.

The intermediate dinitro alcohol compound produced by either of the above-described sequential Michael-Henry reactions has the following formula:

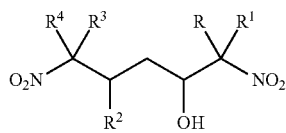

wherein R is independently hydrogen, alkyl, aryl, or —CH₂OH; $R^1$ is independently hydrogen, alkyl, or —CH₂OH; alternatively, R and $R^1$ may be linked together to form a cycloalkyl; $R^2$ is independently hydrogen, methyl, alkyl, phenyl or substituted phenyl; $R_3$ is independently hydrogen, alkyl, phenyl or substituted phenyl, or —CH₂OH; $R^4$ is independently hydrogen, alkyl, or —CH₂OH; and alternatively, $R^3$ and $R^4$ may be linked together to form a cycloalkyl.

In a particular embodiment, the nitroalkane is 2-nitropropane and the α, β-unsaturated aldehyde is either crotonaldehyde or cinnamaldehyde, which would produce a dinitro mono-alcohol compound.

The dinitro alcohol intermediate, whether mono- or poly-alcohol, is then further reduced under hydrogenation conditions in the presence of a suitable catalyst to produce the desired diamino alcohol comprising two amino groups, each of which is bonded to a tertiary carbon atom. Suitable dehydrogenation catalysts include, without limitation, Raney nickel, or a platinum- or palladium-based catalyst, (e.g., platinum or palladium in elemental form or as oxides, with or without supports, e.g., carbon). Other suitable reducing agents include, without limitation, metal/acid combinations, e.g., iron/acetic acid; and aluminum hydrides. An example of a dehydrogenation catalyst system suitable for use in accordance with the present invention is hydrogen gas in combination with any of Raney nickel, platinum or palladium.

The hydrogenation of dinitro alcohol to produce the diaminoalcohol may be performed at pressures between 100 and 1000 pounds per square inch ("psi") and temperatures between 30° C. and 100° C. A solvent may be used, such as, without limitation, tetrahydrofuran or methanol.

EXAMPLES

Example 1

Synthesis of 2,5,6-trimethyl-2,6-dinitroheptan-3-ol
(Dinitro Alcohol Intermediate)

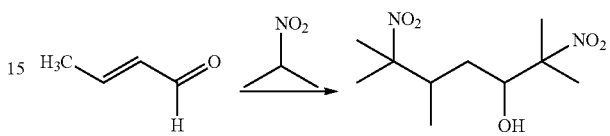

A three neck round bottom flask equipped with a stir bar, thermocouple, dropping funnel capped with nitrogen inlet and condenser was charged with 2-nitropropane ("2-NP") (50 g, 0.56 mols, 5.0 equivalents) and catalytic amount of DBU. The yellow solution was mixed under nitrogen for about thirty minutes. To this mixture was added crotonaldehyde (7.9 g, 9.2 mL, 0.112 moles, 1.0 equivalent) drop-wise over a period of twenty minutes. The addition of crotonaldehyde was done at three different conditions, as follows, and all of them yielded the same results.

Conditions:
A: Dropwise addition of crotonaldehyde when the 2-NP/DBU mixture is at −30° C. and warm to room temperature.
B: Dropwise addition of crotonaldehyde when the 2-NP/DBU mixture is at 20° C. and warm to room temperature.
C: Dropwise addition of crotonaldehyde when the 2-NP/DBU mixture is at room temperature In each case, after complete addition, the reaction was stirred for approximately 5-6 hours at room temperature. During this time, white solid crashed out of the solution. At this point, GC analysis showed the absence of any crotonaldehyde in the reaction mixture. After letting the reaction mixture stir overnight at room temperature and under nitrogen, the white solid was isolated by vacuum filtration and the solid was washed thoroughly with water. The solid was air dried, followed by vacuum drying, at 45° C. The total yield of the desired nitro alcohol was 72% (27.8 g). Nuclear magnetic resonance testing ("NMR") and liquid chromatography (LC) showed that the product was >99% pure. ¹H NMR (CDCl₃): δ 0.82-1.56 (m, 18H), 4.02-4.07 (m, 1H). ¹³C NMR (CDCl₃): δ 14.1, 20.7, 22.5, 23.1, 23.6, 33.5, 37.9, 73.1, 91.8 and 92.1 ppm. The reaction was also run with smaller molar ratio of the unsaturated aldehyde to nitroalkane. Similar results were obtained to the example above, when the ratio of unsaturated aldehyde to nitroalkane was 1:2.9.

Synthesis of 2,6-diamino-2,5,6-trimethylheptan-3-ol
(Diamino Alcohol)

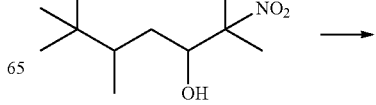

-continued

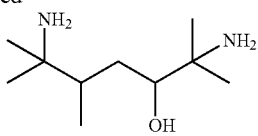

25 g of the nitro alcohol above was dissolved in 200 mL methanol and hydrogenated under in the autoclave at 60° C. using 14.2 g RaNi 3111 as a catalyst and at 600 psi pressure. After workup which included filtration of the catalyst and removal of methanol, approximately 11 g (59% yield) of the low viscous pale green/colorless liquid was obtained. NMR and gas chromatograph-mass spectroscopy ("GC-MS") analysis confirmed the presence of the desired amino alcohol. Chemical ionization mass spectrometry CI-MS showed [M+H]=189 and GC showed that purity of the material to be 94%. The boiling point of the material was approximately 110° C.-120° C. at 0.5-1.5 torr. The pKa of the amines was 10.12. $^1$H NMR (CDCl$_3$): δ 0.48-1.22 (m, 18H), 2.84-2.89 (m, 1H). $^{13}$C NMR (CDCl$_3$): δ 16.8, 25.2, 27.9, 30.8, 34.7, 42.2, 51.8, 52.8 and 77.3 ppm.

The diamino alcohol product of this Example 1 is labeled "CROT-AMP-NH2" in the accompanying figures.

Example 2

Synthesis of 6-methyl-3,7-dinitrononan-4-ol (Dinitro Alcohol Intermediate)

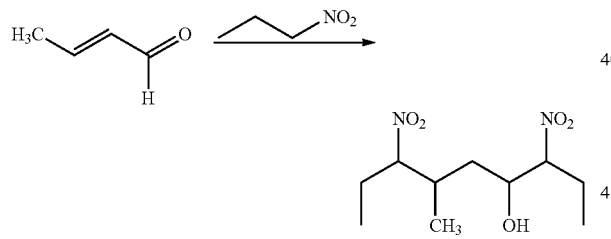

A three neck round bottom flask equipped with a stir bar, thermocouple, dropping funnel capped with nitrogen inlet and condenser was charged with 2-Nitropropane (50 g, 0.56 mots, 5.0 equivalents) and catalytic amount of DBU. The deep yellow solution was mixed under nitrogen for about thirty minutes. To this mixture was added crotonaldehyde (7.9 g, 9.2 mL, 0.112 moles, 1.0 equivalent) drop-wise over a period of twenty minutes. The addition of crotonaldehyde in this case was done at room temperature and during addition, exotherm of about 12° C.-15° C. was observed. After complete addition, the reaction was stirred at room temperature for 6 hours. At this point, GC analysis showed the absence of crotonaldehyde from the mixture. The reaction was let to stir at room temperature overnight and high-performance liquid chromatography (HPLC) analysis showed the presence of only two peaks which correspond to 1-NP which was in excess and the desired product (1CA+2NP adduct). Excess 1-NP was removed by vacuum distillation and the resulting orange viscous liquid was subjected to hydrogenation. This material was about 37.2 g total weight however it still had some 1-NP remaining.

Synthesis of 3,7-diamino-6-methylnonan-4-ol (Diamino Alcohol Intermediate)

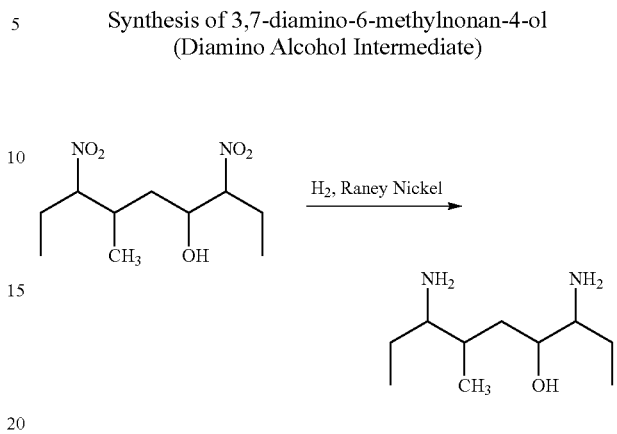

37.2 g of the nitro alcohol above was dissolved in 50 mL methanol and hydrogenated under hydrogen in the autoclave at 60° C., using 14.3 g RaNi 3111 as a catalyst and at 600 psi pressure. After workup which included filtration of the catalyst and removal of methanol, approximately 18 g (64% yield) of the low viscous yellow liquid was obtained. GC-MS analysis confirmed the presence of the desired amino alcohol. CI-MS showed [M+H]=189 and GC showed that purity of the material to be 50%. The rest were low boiling materials. The pKa of the amines was 9.85.

Example 3

Synthesis of 2,6-dimethyl-2,6-dinitro-5-phenylheptan-3-ol (Dinitro Alcohol Intermediate)

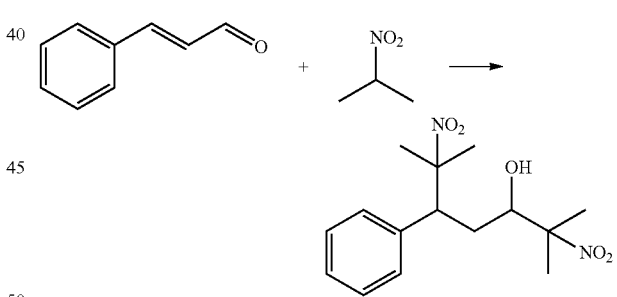

A three neck round bottom flask equipped with a stir bar, thermocouple, dropping funnel capped with nitrogen inlet and condenser was charged with 2-Nitropropane (101.1 g, 1.14 mols, 6.0 equivalents) and catalytic amount of DBU. The yellow solution was mixed under nitrogen for about twenty minutes. To this mixture was added trans-cinnamaldehyde (25.0 g, 0.19 moles, 1.0 equivalent) drop-wise over a period of twenty minutes. During addition of trans-cinnamidehyde to the nitro paraffin, an exotherm of approximately 22° C. was observed. After complete addition, the reaction mixture was heated to 50° C. for 4 h. After the heating time, the mixture was let to cool down slowly to room temperature. When the reaction mixture temperature reached 36.8° C., a pale yellow solid crashed out of the solution. The solid was filtered through a Buchner funnel and washed thoroughly with pentane and ether. The white powder was let to dry under vacuum for 1 hour. The total yield of the desired nitro alcohol was 62% (36 g). NMR showed that the product was >99% pure. $^1$H NMR (CDCl$_3$): δ 1.45-2.27 (m, 15H), 3.52-3.54 (m, 1H), 3.67-3.74 (m, 1H), 7.17-7.34 (m, 5H). $^{13}$C NMR (CDCl$_3$): δ 20.8, 22.4, 23.2, 25.8, 31.3, 50.3, 72.9, 91.5, 91.6, 128.1, 128.7, 129.4, 136.6 ppm.

Synthesis of
2,6-diamino-2,6-dimethyl-5-phenylheptan-3-ol
(Diamino Alcohol)

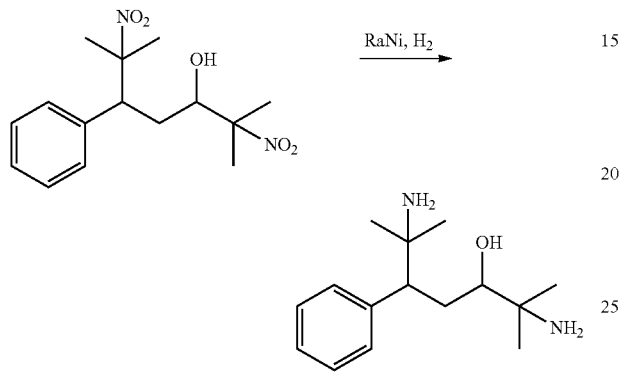

50 g of the nitro alcohol above was dissolved in 300 mL methanol and hydrogenated in the autoclave at 60° C. using 24.3 g RaNi 3111 as a catalyst and at 600 psi pressure. After workup which included filtration of the catalyst and removal of methanol, approximately 40 g (68% yield) of the high viscous pale yellow/colorless liquid was obtained. NMR and GC-MS analysis confirmed the presence of the desired amino alcohol. CI-MS showed [M+H]=251 and GC showed that purity of the material to be 78% straight from the autoclave. The rest of the material seems to be the mono adduct obtained from the reversal of the Henry reaction. The mixture was purified by vacuum distillation and approximately 96.2% purity of the desired material was obtained. The boiling point of the material was approximately 145° C.-155° C. at 0.9-1.1 torr. The pKa of the amines was 9.65. The VOC of the material, as determined by modified EPA Method 24, is 4.4%. $^1$H NMR (CDCl$_3$): δ 0.91-0.99 (m, 12H), 1.67-1.81 (m, 3H), 2.71-2.76 (m, 2H), 7.08-7.23 (m, 5H). $^{13}$C NMR (CDCl$_3$): δ 24.6, 27.9, 28.3, 29.8, 31.6, 51.8, 52.6, 54.2, 75.9, 126.3, 127.8, 129.4, 142.0 ppm.

The diamino alcohol product of this Example 3 is labeled "CINNAM-AMP-NH2" in the accompanying figures.

The diamino alcohol compounds prepared in Examples 1 and 3 are compared with commercially available amino compounds which are currently used in aqueous coating formulations for dispersion of pigments. The following list provides the labels and sources of the known and commercially available amino compounds used for comparison:

AMP 95=amine compound (2-amino-2-methyl-1-propanol), available from ANGUS Chemical Company, a wholly owned subsidiary of the Dow Chemical Company of Midland, Mich., USA, that is useful as a dispersant in coating formulations.

N-Butyl-diethanolamine (NBDA)=Also called Vantex® T an amine compound available from Taminco of Ghent, Belgium (and Atlanta, Ga., USA), advertised as useful as a dispersant having low VOC content and low odor for coatings formulations.

AEPD VOX 1000=amine compound, available from ANGUS Chemical Company, a wholly owned subsidiary of the Dow Chemical Company of Midland, Mich., USA, that is useful as a dispersant in coating formulations with reduced VOC content and odor.

The bar graphs of the FIGURE show how the VOC content and pKa of each of the diamino alcohol compounds of Example 1 (CROT-AMP-NH2) and Example 3 (CINNAM-AMP-NP2) compare with those of the commercial amines.

What is claimed is:

1. A process for the production of a diamino polyol compound having the formula:

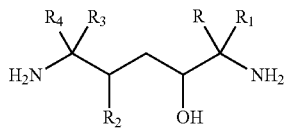

wherein each of the two amino (—NH$_2$) groups is bonded to a tertiary atom, R and R$_3$ are the same as each other and are each a, alkyl, aryl, or —CH$_2$OH; R$_1$ and R$_4$ are the same as each other and are each, alkyl, aryl, or —CH$_2$OH; alternatively, R and R$_1$ may be linked together to form a cycloalkyl; R$_2$ is independently alkyl, or phenyl; and alternatively, R$_3$ and R$_4$ may be linked together to form a cycloalkyl, said process comprising:

(A)(i) reacting (1) a primary nitroalkane and (2) an α,β-unstaturated aldehyde, at a molar ratio of 2:1, and in the presence of an organic catalyst, and under conditions in which Michael addition and nitro-aldol (Henry) reaction, between the (1) primary nitroalkane and the (2) α,β-unstaturated aldehyde, occur sequentially, Michael reaction first, to form a dinitro alcohol;

(A)(ii) further reacting the resulting dinitro alcohol with (3) an aldehyde to form a dinitro poly-alcohol compound; and (B) reducing the dinitro poly-alcohol compound of step (A)(ii) to the corresponding diamino polyol under hydrogenation conditions, in the presence of a catalyst.

2. The process according to claim 1, wherein the catalyst used in said hydrogenation (B) step comprises Raney nickel.

3. The process according to claim 1, wherein the (1) primary nitroalkane is nitroethane or 1-nitropropane or nitromethane, followed by reaction with (3) formaldehyde.

* * * * *